(12) United States Patent
Hohmann et al.

(10) Patent No.: US 8,220,623 B2
(45) Date of Patent: Jul. 17, 2012

(54) CONTAINER

(75) Inventors: Arno Hohmann, München (DE); Marc Peuker, Schondorf (DE)

(73) Assignee: 3M Innovative Properties Company, St. Paul, MN (US)

( * ) Notice: Subject to any disclaimer, the term of this patent is extended or adjusted under 35 U.S.C. 154(b) by 1351 days.

(21) Appl. No.: 11/669,212

(22) Filed: Jan. 31, 2007

(65) Prior Publication Data

US 2007/0187265 A1    Aug. 16, 2007

(30) Foreign Application Priority Data

Feb. 3, 2006   (EP) ..................................... 06002283

(51) Int. Cl.
*B65D 25/08*   (2006.01)

(52) U.S. Cl. ........................ 206/219; 206/822

(58) Field of Classification Search .................. 206/219, 206/222, 221, 822
See application file for complete search history.

(56) References Cited

U.S. PATENT DOCUMENTS

| | | | | |
|---|---|---|---|---|
| 927,826 A * | 7/1909 | Breitmeyer | .................... | 206/218 |
| 2,559,231 A * | 7/1951 | Seemar | .......................... | 604/415 |
| 2,753,868 A * | 7/1956 | Seemar | .......................... | 604/415 |
| 3,039,644 A * | 6/1962 | Lefcort | .......................... | 220/501 |
| 3,339,716 A * | 9/1967 | Taylor | ........................... | 206/219 |
| 3,618,751 A * | 11/1971 | Rich | .............................. | 206/219 |
| 4,836,370 A | 6/1989 | Bosshard | ..................... | 206/222 |
| 5,246,142 A * | 9/1993 | DiPalma et al. | .............. | 222/129 |
| 5,394,980 A * | 3/1995 | Tsai | .............................. | 206/63.5 |
| 5,616,337 A * | 4/1997 | Kasianovitz et al. | ......... | 424/414 |
| 5,678,709 A * | 10/1997 | Holley et al. | ................. | 215/11.4 |
| 5,928,213 A * | 7/1999 | Barney et al. | ................. | 604/410 |
| 6,079,871 A * | 6/2000 | Jonas et al. | .................... | 366/336 |
| 6,105,761 A | 8/2000 | Peuker et al. | ................. | 206/229 |
| 6,386,872 B1 * | 5/2002 | Mukasa et al. | ................. | 433/90 |
| 6,394,803 B1 | 5/2002 | Salz et al. | ....................... | 433/49 |
| 6,474,467 B1 * | 11/2002 | Kurdian | ........................ | 206/222 |
| 6,769,539 B2 * | 8/2004 | Stern et al. | .................... | 206/222 |
| 6,857,805 B2 | 2/2005 | Galehr et al. | .................. | 401/125 |
| 2002/0066680 A1 * | 6/2002 | Stern et al. | .................... | 206/222 |
| 2003/0026876 A1 | 2/2003 | Albuja et al. | .................. | 426/120 |
| 2004/0134815 A1 | 7/2004 | Discko, Jr. | ..................... | 206/361 |
| 2005/0178677 A1 * | 8/2005 | Morrow | ........................ | 206/219 |
| 2006/0191805 A1 * | 8/2006 | Vogel et al. | ..................... | 206/222 |
| 2008/0083348 A1 * | 4/2008 | Kuo et al. | ....................... | 106/35 |

FOREIGN PATENT DOCUMENTS

| | | |
|---|---|---|
| EP | 0 124 952 | 11/1984 |
| EP | 0 895 943 | 2/1999 |
| EP | 1 106 147 | 6/2001 |
| EP | 1 576 934 | 9/2005 |

\* cited by examiner

*Primary Examiner* — Jacob K Ackun

(74) *Attorney, Agent, or Firm* — Peter L. Olson

(57) ABSTRACT

A container having a container bottom and a container wall defining a chamber, wherein a portion of the container wall comprises at least one compartment for accommodating a component.

22 Claims, 5 Drawing Sheets

CONTAINER

CROSS-REFERENCE TO RELATED APPLICATIONS

This application claims priority from European Patent Application No. 06002283.7, filed Feb. 3, 2006.

FIELD OF THE INVENTION

This invention relates to a storage container for single component materials or compositions that are made of two or more components. The container stores one or more components until a quantity of the composition is needed for use. In case of two or more components, the components are stored in isolation from each other until needed for use.

BACKGROUND OF THE INVENTION

Many useful compositions are made of two components that are not normally mixed together until immediately prior to the time that a quantity of the composition is needed for use. For example, the components of epoxy-based adhesives are stored separately from each other, because once the components come into contact with each other a chemical reaction is initiated that eventually turns the mixed composition into a hardened mass. For that reason, epoxy-based adhesives are widely available in packages that include two compartments or two separate containers that keep the components of the adhesive initially isolated from each other.

In recent years, there has been increased interest in "single use" containers for compositions made of two components that are initially kept apart from each other. Such containers typically avoid the need to measure out separate quantities of each component before mixing. These containers also help assure that the components, when mixed, are present in the desired ratio of the resulting composition. Additionally, if the components are mixed together within the container, the need for a mixing well, pad, container or other type of mixing structure is avoided.

Single use containers for multiple component compositions are especially convenient for storing medical and dental compositions, because the container along with the applicator can be disposed of after use for a single patient. In this manner, the risk of transferring an infectious disease from one patient to another is substantially reduced.

Oftentimes, only a relatively small quantity of the composition is needed at any one time, and the smaller "single dose" or "single use" containers help ensure that a freshly-mixed batch of the composition is available when needed.

Reference is made to EP-A-0 895 943, EP-A-1 106 147, EP-A-1 576 934, U.S. Pat. No. 4,836,370, and U.S. Pat. No. 6,857,805 which generally relate to package assemblies.

SUMMARY OF THE INVENTION

The present invention is related to an improved container for storing material, preferably dental material. According to a preferred embodiment, the present invention relates to an improved container for single components or compositions that are made of two or more components. The container is especially suitable for single-use applications, such as those found in the field of dentistry. The container may be used for mixing of the components in addition to storage of the components, such that the need to transfer the components to a separate container or surface for mixing is unnecessary.

The present invention is directed in one aspect to a container having a container bottom wall and a container side wall. The container bottom wall and the container side wall define a chamber. A portion of the container wall (bottom wall and/or side wall) comprises at least one compartment for accommodating a component. The container wall preferably comprises two compartments which are preferably arranged side-by-side. Alternatively the compartments can be arranged preferably in the container side wall vertically spaced from each other, at circumferentially opposite areas, or at any other area of the container side wall, for example.

The container further comprises a base for a supporting the container on a surface, such as a dentist's tray.

The container side wall extends upwards from the container bottom wall, and is preferably substantially perpendicular to the container bottom wall. The container is preferably substantially U-shaped, N-shaped, or M-shaped in cross section. In the first case, the container bottom wall is substantially flat or concave, whereas in the second case the container bottom wall is inclined with respect to the container side wall. In the third case, the container bottom wall is inclined and forms a V.

The one or more compartments extend into the container wall, and may be formed by recesses within the container wall which are integrally manufactured with the container. Preferably, a portion of the container wall protrudes from the remainder of the container wall to form the one or more compartments. The compartments are preferably arranged such that the stored component tends to at least in part flow out of the compartment when the container stands (or is placed) with its base on a horizontal surface. For example, the compartment is a recess of e.g. hemispherical, conical, pyramidal or any other three-dimensional shape. Furthermore the recess may be a cavity extending along an inclined axis, the cavity having e.g. a circular, rectangular or any other cross-sectional shape.

Alternatively, the at least one compartment may be formed as a separate insert that is connected to the container wall by welding or by means of a press-fit or an adhesive, for example. In that case, the compartment may be made of a material different than the container, if desired.

The one or more compartments are closed with a removable cover to seal the components in the compartments. The removable cover may be a closure film or foil (for example made from a plastic film consisting of at least one film layer or of a multi-layer foil including at least one plastic film and a metallic foil), and is preferably peelably or hingedly (for example as a film hinge) attached to the container. The removable cover is preferably heat sealed to the container wall. The removable cover comprises a first portion that is sealed to the container wall at least around the circumference of the compartment. Furthermore, the cover comprises at least a second portion extending from the first portion, e.g. to form a grip portion which a user can grasp to remove the cover.

In an alternative embodiment the cover is a non-removable cover which is pierced to open the compartments (e.g. by use of an applicator such as a brush or dental instrument). It is also possible to use the embodiments having a removable cover in the same manner.

According to a preferred embodiment of the present invention, the removable cover is attached to the container wall to cover the compartment so that the second portion of the cover is oriented closer to the bottom wall of the container than the first portion of the cover. The first portion of the removable cover closes the at least one compartment and the second portion is folded backwards over the first portion. The second portion may be grasped by a user to remove the cover. Preferably, the fold is located between the lower edge of the compartment and the corner or junction between the container side wall and the container bottom wall. In case of a multi-compartment container, each compartment is preferably closed with a separate removable cover, although a single such cover could enclose multiple compartments.

According to an alternative, the removable cover is peeled or otherwise removed beginning at one side of the compartment and progressing toward the other. In this case, the first portion of the removable cover closes the at least one compartment and the second portion may be folded over the first portion. The second portion may be grasped by a user to remove the cover. Preferably, the fold is located between one side edge of the compartment and the edge of the container wall. As a further alternative, the removable cover comprises a free end at one corner of the container (preferably the upper left or right corner above the compartment), and this free end may be grasped by a user for removing the cover. As a further alternative the free end is one side of the cover, preferably the upper side above the at least one compartment. As an option or additionally the right, left or lower side may comprise a free end which is graspable by a user. As still a further alternative, the cover comprises a cord, string, or strip, which when pulled tears or removes the cover to open the compartment.

It is further preferred that the container wall comprises a scraper for removing substance that adheres to the cover during removal of the cover. The scraper may be formed, for example, as a slit in the container wall, and the second portion of the removable cover extends through the slit.

It is also preferred that the container wall further comprises a longitudinal through passageway such as a channel that is adapted to accommodate the part of the removed cover that has contacted material stored in the compartment.

In an alternative embodiment the compartment comprises a pocket for retaining a portion of material from flowing out when the cover is removed. In case the embodiment has two or more compartments a portion of the materials contained in the compartments flow into the chamber of the container upon removing the cover and contact each other or mix. The other portion of the materials remain in the pockets of their individual compartments. This provides a user with access to a mixture of the materials as well as individual unmixed materials when the container has been opened for use.

As an alternative to the peelable foil, the removable cover may be a cap or plug.

The container can store in the compartment a pre-determined quantity of a component, either in liquid, paste, or solid (e.g. powder) form, and the chamber formed by the container wall can conveniently serve as a place to mix the composition once the second component has been added to the first component. The at least one compartment of the container is preferably pre-filled with at least one dental substance. The cover encloses the dental substance in the compartment.

The chamber of the container may also be used to store a component. In this embodiment the chamber could also be partially closed with the removable cover.

In an alternative embodiment a portion of the container bottom wall comprises at least one compartment for accommodating a component. In this alternative embodiment the container bottom wall preferably comprises at least two compartments which are preferably arranged spaced from each other and located at any place of the container bottom wall. As an option each of the container bottom wall and the container side wall comprise at least one compartment.

In an embodiment a plurality of containers are combined to be supplied as packs. In this case, the individual containers may be manufactured as one piece containing multiple containers (for example a bar of multiple containers) which can be separated, e.g., because of perforations or other weakened portions to facilitate use. In an alternative embodiment the containers can be supplied individually.

The container can be inexpensively made of a plastic material, for example by injection molding, or by deep drawing a plastic or metal film or sheet. As a result, the cost of the container is relatively low.

The present invention is also directed in another aspect to a kit comprising a container of the first aspect and at least one mixing device or applicator. The applicator is preferably a brush. The kit may also comprise a plurality of items selected from the group comprising containers and applicators. For example, the containers are provided in packs containing multiple items selected from the group comprising containers and applicators. It may be provided that those items initially are connected to each other and can be separated, e.g., by perforations to facilitate use.

According to a further aspect the invention is directed to a method of manufacturing a container of the type described above by injection molding, wherein the compartment and the chamber of the container are integrally molded (molded in a single piece) by a one-piece portion of the mold. This means that the one-piece portion is a piece within the mold, e.g. a movable core, comprising the negative shape of the compartment and the negative shape of the chamber of the container. In this context "one-piece" means that the piece may consist of one part or may be assembled from several parts but acts as one piece during the intended use of the mold. Integrally molding of the compartment and the chamber enables manufacturing by use of one mold in one step, which otherwise would require an additional mold and assembly step, while the use of a one-piece portion of the mold to form both parts provides a minimized amount of movable cores in the mold. Both aspects minimize costs for manufacturing and investment.

BRIEF DESCRIPTION OF THE DRAWINGS

Preferred embodiments of the invention are described in more detail below with reference to the attached drawings, which are by way of example only.

DETAILED DESCRIPTION OF PREFERRED EMBODIMENTS

Figure 2:
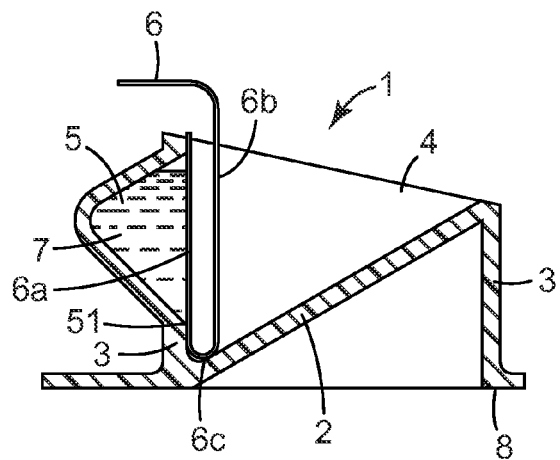
FIG. 2 is a schematic cross-sectional view of the closed container of FIG. 1.
Figure 12:
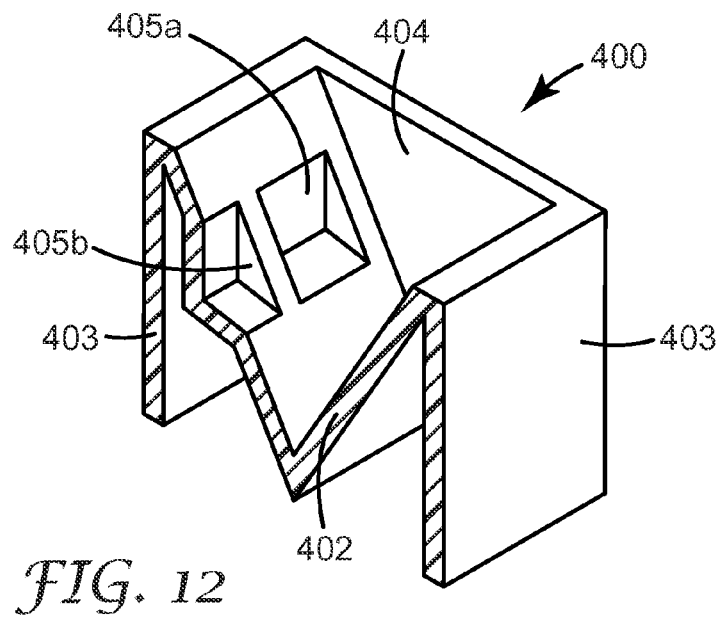
FIG. 12 is a perspective cross-sectional view of an alternative embodiment.

FIG. 2 is a schematic cross-sectional view of a container 1 according to a preferred embodiment of the present invention. In this embodiment, the container 1 is substantially N-shaped and has a container side wall 3 and a container bottom wall 2 that is inclined with respect to the container side wall 3. The container 1 could instead be generally U-shaped, with a container bottom wall that is substantially perpendicular to the container side wall(s), generally V-shaped without a container bottom that contacts the contents of the container but with a base that supports the container, or of other suitable shapes. A V-shaped (or M-shaped) alternative is shown in FIG. 12.

The container 1 further comprises a base 8 for supporting the container on a surface. Base 8 may define a base plane. Such a base may be provided by, e.g. individual "feet" or a flat surface at the bottom of the container.

Figure 1:
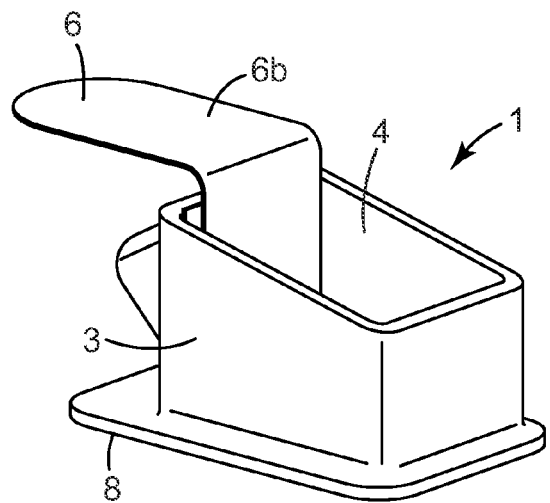
FIG. 1 is a perspective view of a container according to an embodiment of the invention, having the compartment closed by a foil.

As shown in FIG. 1, which is a perspective view of the container of FIG. 2, three sides of the container side wall 3 and the inclined container bottom wall 2 define a chamber 4 within the container 1. Although in the illustrated embodiments multiple container walls may be shown, in other embodiments the container may include only one side wall (in the case of a cylindrical container), or two side walls.

Figure 3:
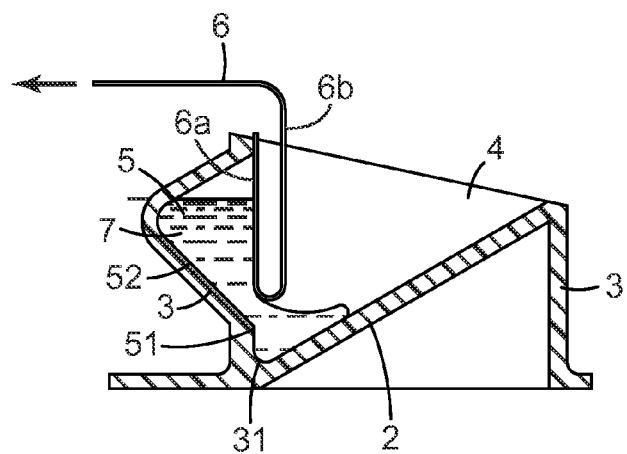
FIG. 3 is a schematic cross-sectional view of the container of FIG. 1 where the compartment is partially opened.

The container side wall 3 comprises a compartment 5 (shown in FIGS. 2 and 3, which could in other embodiments be provided in container bottom wall 2). A predetermined quantity of a material 7, for example in liquid, paste, or solid (e.g. powder) form, can be stored in the compartment 5. As shown in FIGS. 2 and 3, the compartment is preferably arranged in the container side wall, or a portion of the container side wall protrudes from the remainder of the container side wall 3 to form a compartment 5. The compartment 5 is preferably shaped such that the material stored in the compartment 5 tends to at least in part flow out of the compartment 5 when the container side wall 3 in FIGS. 1-3 is in substantially vertical position, i.e., when the container 1 stands or is placed with its base 8 on a horizontal surface. For example, a downward inclination of the bottom wall 2 of compartment 5 as shown in FIGS. 2 and 3 is preferred so that the material 7 stored in the compartment tends to flow downward under the force of gravity. This is shown in FIG. 3. In embodiments where the compartment 5 is provided in a container bottom wall 2, the container 1 may be adapted so that any material added to the container (for example from a compartment in a side wall, or added by a user) tends to flow into the compartment 5.

The compartment 5 preferably has at least one inner surface 52 (see FIG. 3) that adjoins the surface of the container side wall 3 on the sides of the compartment 5. It may also adjoin the surface of the container side wall 3 at the lower edge of the compartment. Alternatively, the inner surface 52 may meet directly with the lowest point 31 of the chamber.

The inner surface 52 of the compartment 5 comprises at least one lowest point 51 which is preferably nearest the base plane.

It is further preferred that the compartment is located at a height relative to the base of the container such that the opening of the compartment is at least in part within the chamber of the container.

The lowest point 51 of the inner surface 52 of the compartment 5 is preferably at the same level as or above the lowest point of the opening of the compartment 5, so that all material 7 in the compartment 5 can be emptied from it more easily.

To keep the material 7 in the compartment 5 until it is needed for use, the compartment 5 is closed by a removable cover 6, such as a sealing foil. Removable cover 6 consists of a first portion 6a that covers the compartment. The first portion 6a of the removable cover 6 is sealed to the container wall 3 at least around the circumference of the compartment 5, which preferably provides a hermetic seal to protect the contents of the compartment 5. A second portion 6b of the cover 6 is graspable by the user so that the user can remove the cover 6 as shown in FIG. 3. In FIG. 2, the first portion 6a closes the compartment 5, and the second portion 6b is folded backwards (although an actual fold is not required) and extends upward. The junction 6c between the first portion 6a and the second portion 6b is located between the lower edge 51 of the compartment 5 and the edge 31 between the container wall 3 and the container bottom 2, in the illustrated embodiment. Although in FIG. 3 the removal force is shown as extending toward the left, the force could be in any direction that permits removal of the cover 6, including vertically, toward the right (in FIG. 3), or in any other direction.

Figure 4:
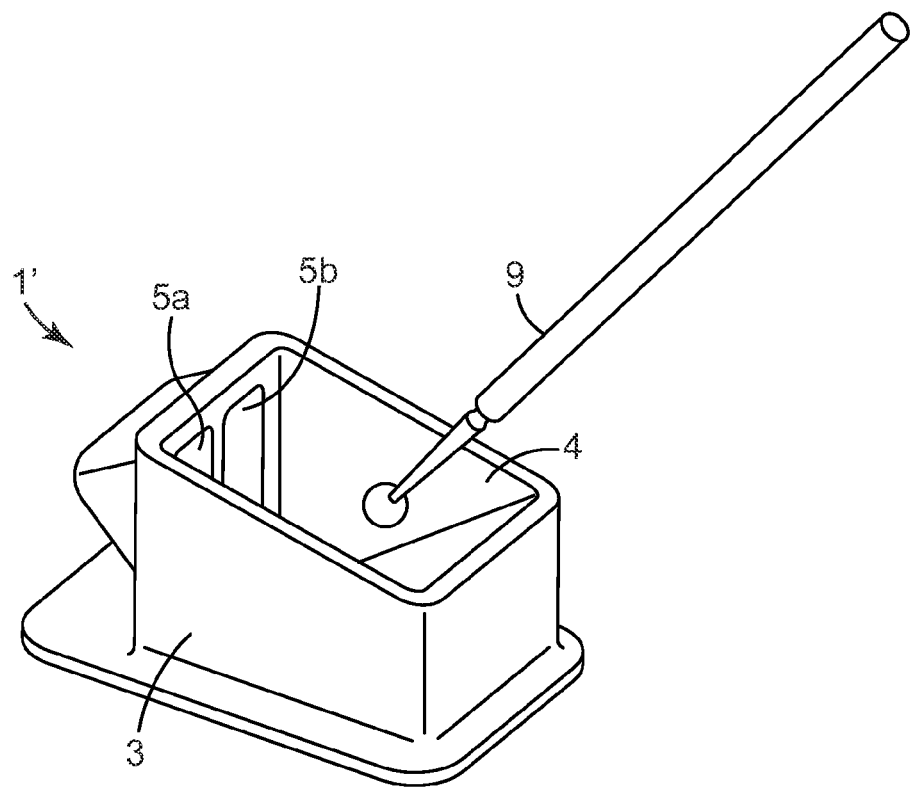
FIG. 4 is a perspective view of the opened container, shown together with an applicator.

FIG. 4 shows the container 1' where the cover has been completely removed. The container 1' shown in FIG. 4 comprises two compartments 5a and 5b that are arranged side by side, in order to accommodate two materials, which may be the same or different. Once the cover is removed, as shown in FIG. 4, the two materials flow into the chamber 4 due to the inclination of the bottom walls of the compartments 5a, 5b. The two materials can then be mixed in the chamber 4 with a mixing device or an applicator 9.

The compartments 5a and 5b may also be arranged vertically, with one compartment positioned above the other. In this case the material stored in the upper compartment flows through the lower compartment once the cover is removed, preferably to wash out all of the material stored in the lower compartment. This is especially advantageous if the lower compartment contains a small amount of a material relative to the other material(s). With such an arrangement of multiple compartments, the cover can be removed from only one compartment, or from two or more compartments, depending on when the individual materials are needed.

It may also be provided that the compartments 5a and 5b are closed by two separate covers. This is advantageous if the two components can be used when mixed with each other or as separate components. Instead of two separate covers, as an alternative a cover comprising a weakened portion (e.g. a line of perforations, or a slit) can be used to allow easy removal of the whole cover as well as to allow the individual compartments to be opened independently from each other.

Figure 5:
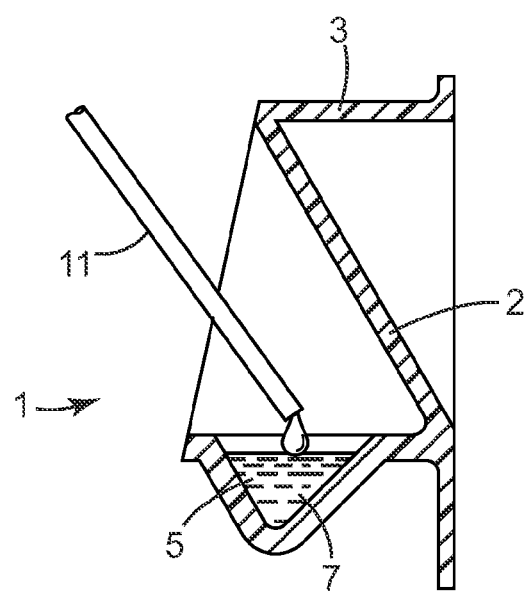
FIG. 5 is a schematic cross-sectional view showing the container of the invention when it is filled.

FIG. 5 shows a method of filling the compartment 5 during the manufacturing stage. Here, container 1 is brought into an upright position so that the container side wall 3 is essentially horizontal, and the compartment 5 is positioned to receive material 7. A dispensing device 11 can then be used to fill material 7 into compartment 5 as shown in FIG. 5.

Figure 6:
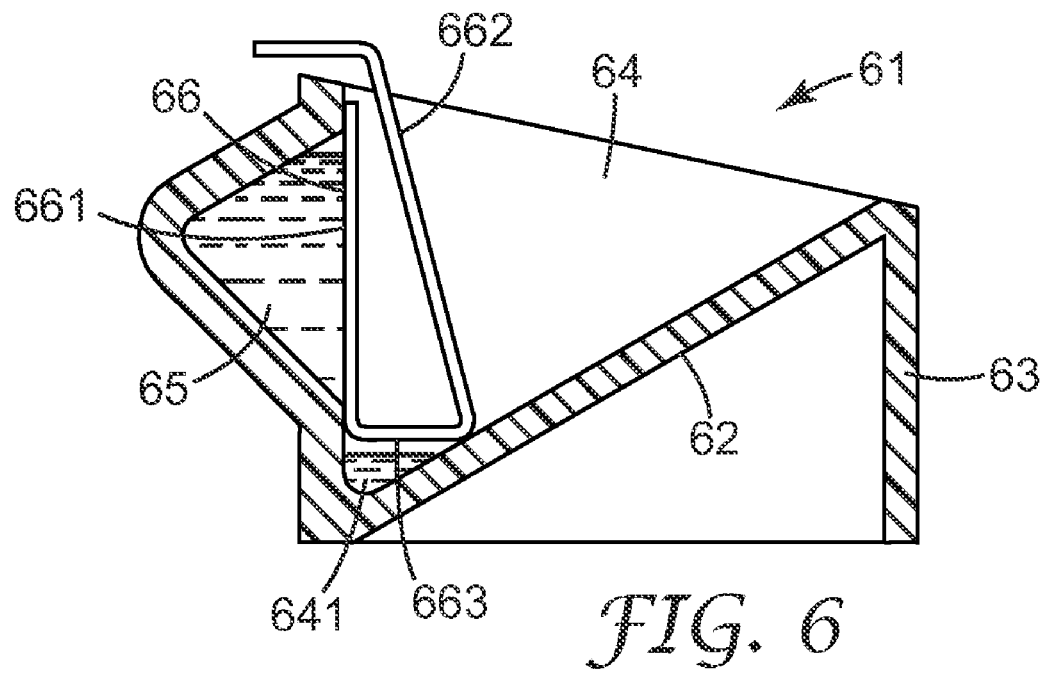
FIG. 6 is a cross-sectional view of a container according to an alternative embodiment of the invention, having the compartment and a part of the chamber of the container closed by a foil.
Figure 7:
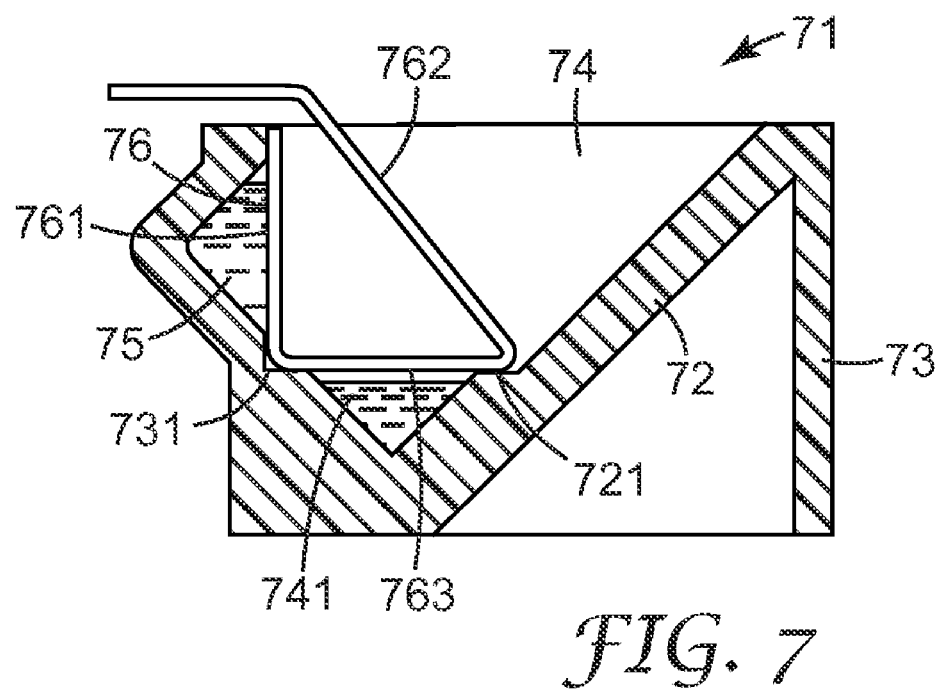
FIG. 7 is a cross-sectional view of an alternative embodiment of the container shown in FIG. 6.

FIGS. 6 and 7 show alternative embodiments of the container. The containers 61 and 71 shown in FIGS. 6 and 7 comprise a container side wall 63, 73 and an inclined container bottom wall 62, 72 that define a chamber 64, 74 within the container 61, 71. Like in the embodiment shown in FIGS. 1 to 5, the container side wall 63, 73 comprises at least one compartment 65, 75. The compartment is closed by a removable cover 66, 76. In this embodiment, however, the removable cover 66, 76 also partially encloses the compartment(s) formed by the container side wall and bottom wall in FIG. 6, or in the bottom wall 72 in FIG. 7. The removable cover 66, 76 comprises a first portion 661, 761 that encloses the compartment, and a second portion 662, 762 that extends upward and can be grasped by a user. In addition, the removable cover comprises an intermediate portion 663, 763 between the first and second portions. The intermediate portion covers the bottom wall compartment 641, 741 of the container chamber 64, 74, allowing a storage of an additional material.

In addition to what is shown in FIG. 6, the container 71 of FIG. 7 comprises a recess or step 721 in the inclined container bottom wall 72, and a recess or step 731 in the container side wall 73. The two recesses or steps are located to form the chamber bottom wall compartment 741, and provide an attachment and sealing surface for the removable cover 76.

Figure 8:
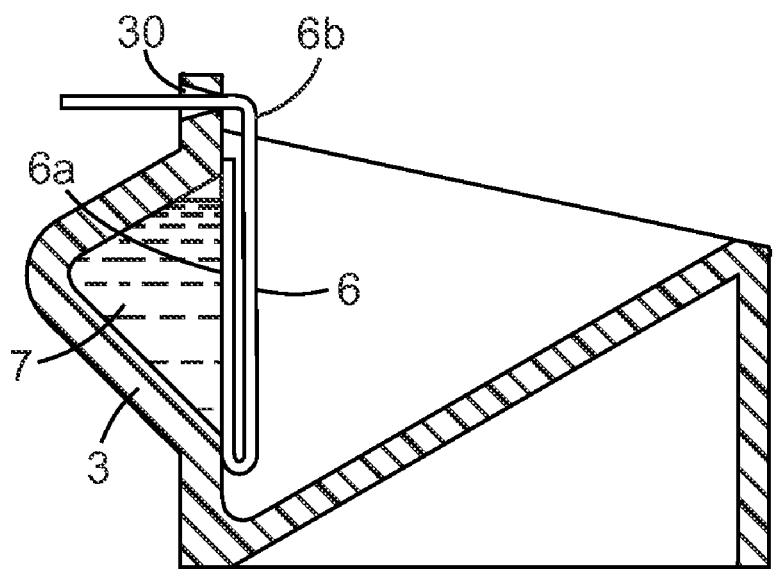
FIG. 8 is cross-sectional view of a container according to an alternative embodiment of the invention, having a scraper formed in the container wall.

As shown in FIG. 8, the container wall 3 preferably comprises a scraper 30 for removing substance that adheres to the cover 6 during removal of the cover 6. The scraper 30 is formed, for example, as a slit in the container wall 3, and the free end of the second portion 6b of the removable cover 6 extends through the slit 30.

Figure 9:
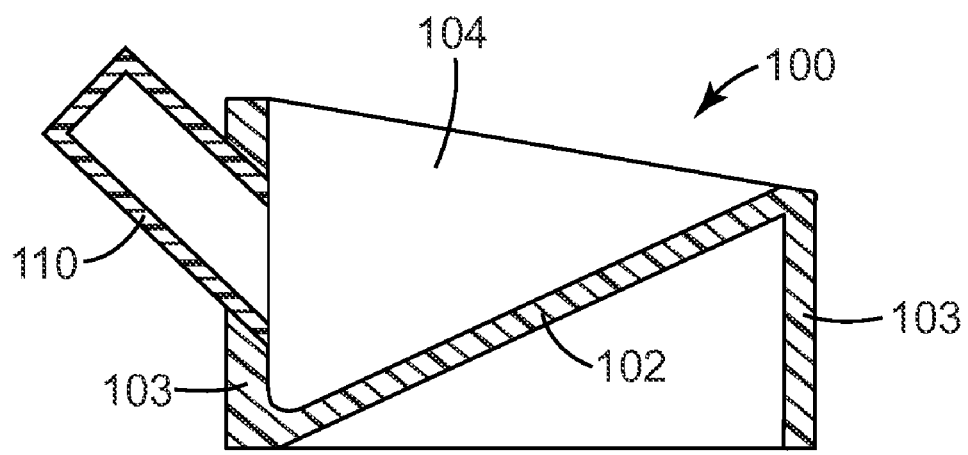
FIG. 9 is a schematic cross-sectional view of a container according to another embodiment of the invention.

FIG. 9 shows an alternative embodiment of the present invention. Container 100 shown in FIG. 9 comprises a container side wall 103, and an inclined container bottom wall 102, similar to the container 1, 1', 61, and 71 shown in FIGS. 1 to 8. However, in the embodiment of FIG. 9, the compartment for the material to be stored is formed by a separate insert 110 that is connected to the container side wall at a respective opening by press-fit or an adhesive, for example. In that case, the compartment may be made of a material different than the container, if desired. E.g. the compartment may be made of a material which provides good barrier properties to reduce the risk that the stored material escapes through the walls of the compartment by permeation. Materials providing such properties are in some cases quite expensive. In such cases this provides the option to only make the compartment of the expensive material while the rest of the container is made of a cheaper material.

Furthermore the structure of this alternative embodiment as shown in FIG. 9 provides a higher degree of freedom in design as the individual parts can be manufactured (preferably molded) separately.

Figure 10:
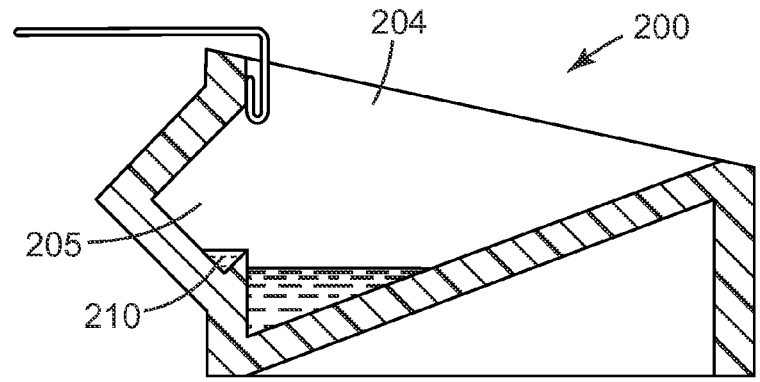
FIG. 10 is a schematic cross-sectional view of a container according to another embodiment of the invention, having a pocket within the compartment for retaining an amount of material.

FIG. 10 shows an alternate embodiment of the present invention. Container 200 shown in FIG. 10 has a compartment 205 comprising a pocket 210. Pocket 210 forms a part of the volume of the compartment. When the cover is removed from this container, only a portion of the material contained in the compartment 205 flows into chamber 204, and the other portion is retained in pocket 210. In case the container comprises at least two compartments, a portion of the materials contained the compartments flow into chamber 204 and contact or mix with each other while an amount of unmixed material remains in the pockets. This is of advantage, for example when the user needs to apply the individual materials as they are stored in the individual pocket(s), as well as a mixture of them.

Figure 11:
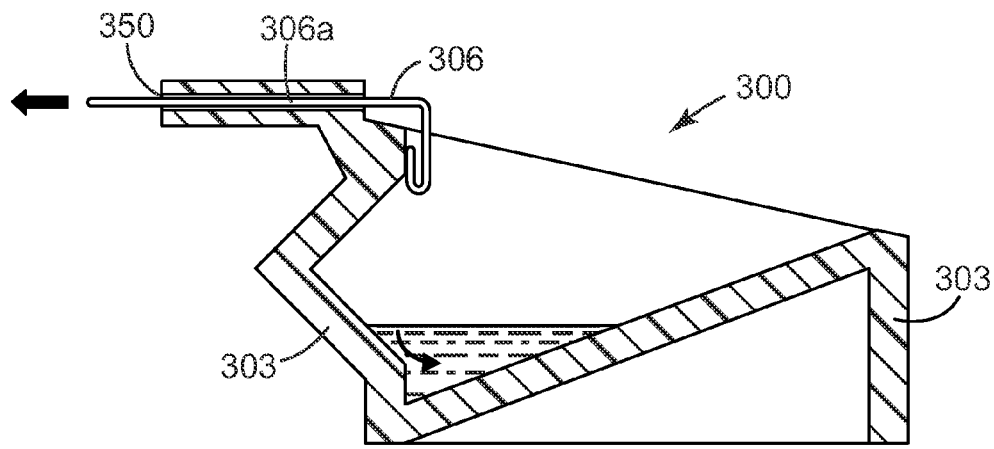
FIG. 11 is a schematic cross-sectional view of a container according to another embodiment of the invention, having a through passageway for accommodating the contaminated part of the removed cover.

FIG. 11 shows another embodiment of the present invention, comprising a container wall 303 further comprising a through passageway 350 that is adapted to the removable cover 306 for accommodating the contaminated part of the removed cover 306a. This may be especially useful if the material stored in a compartment would irritate human skin, eyes, and so on. However, as it is in general desirable that any container can be opened and used without unintentionally getting in touch with the material stored in it, this embodiment provides that the user cannot touch the part of the cover having been in contact with the material stored in the compartment.

It is shown in FIG. 11 (and also, for example, in FIG. 6 that the area where the materials can be mixed together may include a part of the compartment and/or pocket. In other words, the material stored in the compartment, when released into the mixing area, may not entirely be outside of the compartment or pocket, which means that not all of the material must always completely flow out of the compartment and/or pocket.

FIG. 12 shows a further embodiment of the invention. The container 400 of this embodiment is substantially M-shaped in cross section, having container side wall 403 and container bottom wall 402 forming chamber 404. In this embodiment, the V-shaped container bottom wall 402 comprises at least one compartment (in FIG. 12 two compartments 405a and 405b are shown).

The container of the invention as shown in FIGS. 1 through 12 is advantageous as it can be easily filled in an upright position (as shown in FIG. 5), and then sealed by the removable cover. The container can then be repositioned for use (see, for example, FIG. 4). Once the cover is removed, the material or components flow into the mixing chamber 4, and can then easily be mixed by the user and applied wherever needed.

Examples of materials that can be used in a container of this type include dental materials like bondings, resins, conditioners, etchants, sealants, whitening agents, fluorides, and desensitizers, as well as caries treatment solutions, caries indicator solutions or dental diagnostic solutions. Other materials like non-dental adhesives, resins, conditioners or other two-component materials could be used in the container. In this context flowable materials and flowables include fluids as well as free flowing powders and granules.

An additional advantage of providing two compartments, or one compartment with a pocket, is to provide the user with an option to add in additional material to suit her or his preference. In other words, if for a certain mixture some dentists prefer a less viscous mix, they would use 90% of the (solid) material (stored in a first compartment, for example, or in the non-pocket area of a compartment), whereas a dentist who prefers a more viscous mix would use 100% of the (solid) material (stored in first and second compartments, for example, or in the entire volume of a compartment with a pocket). This might also be true if the mixture would be different if used for example at high altitude, or under other varying environmental conditions (heat, humidity, etc.).

The present invention has now been described with reference to several embodiments thereof. It will be apparent to those skilled in the art that many changes can be made in the embodiments described without departing from the scope of the present invention. Thus the scope of the present invention should not be limited to the structures described in this application, but only by structures described by the language of the claims and the equivalents of those structures.

The invention claimed is:

1. A container having a container bottom wall and a container side wall defining a chamber, the container side wall extending substantially upwards, wherein the container bottom wall is inclined with respect to the container side wall, wherein a portion of the container side wall comprises a compartment, said compartment extending laterally into the container side wall and containing a component, the compartment being closed with a removable cover for sealing the component within the compartment, the removable cover comprising a first portion being sealed to the container wall around the circumference of the compartment to close the compartment, and a second portion, extending from the first portion, for being grasped by a user, wherein the compartment is shaped such that the component can flow into the chamber once the cover is removed.

2. The container of claim 1, wherein the container bottom wall is flat.

3. The container of claim 1, wherein the container is substantially N-shaped in cross section.

4. The container of claim 1, wherein the stored component tends to at least in part flow out of the compartment when the container wall is vertical.

5. The container of claim 1, wherein the removable cover is a closure film or foil.

6. The container of claim 5, wherein the removable cover is peelably or hingedly attached to the container.

7. The container of claim 5, wherein the removable cover is made from a type of film or foil selected from among plastic films, metallic foils and compositions thereof.

8. The container of claim 1, wherein the removable cover is heat sealed to the container wall.

9. The container of claim 8, wherein the first portion of the removable cover closes the at least one compartment and the second portion is folded backwards over the first portion.

10. The container of claim 9, wherein the fold is located between the lower edge of the compartment and the edge between the container side wall and the container bottom wall.

11. The container of claim 1, wherein the container comprises more than one compartment, and each compartment is closed with a separate removable cover.

12. The container of claim 1, wherein the component is a dental substance.

13. The container of claim 12, wherein the cover encapsulates the dental substance in the compartment.

14. The container of claim 1, made of a plastic material.

15. The container of claim 14, wherein the container is formed by injection molding.

16. The container of claim 15, wherein the container is manufactured by deep drawing a film and/or foil.

17. A container having a container bottom and a container wall defining a chamber, wherein the container wall extends substantially upwards, and wherein the container bottom is inclined with respect to the container wall so that the container is substantially N-shaped in cross-section, wherein a portion of the container wall comprises two compartments for accommodating two components, said compartments being arranged side-by-side and extending laterally into the container wall, wherein the stored components tend to at least in part flow out of the compartment when the container wall is vertical, the two compartments being closed with a removable cover, the removable cover comprising a first portion being sealed to the container wall at least along a circumferential line around the compartments, and a second portion, extending from the first portion, for being grasped by a user, and wherein the first portion of the removable cover closes the at least one compartment and the second portion is folded backwards over the first portion.

18. The container of claim 17, wherein the component is a dental substance.

19. The container of claim 18, wherein the cover encapsulates the dental substance in the compartments.

20. The container of claim 17, wherein the first portion of the removable cover closes the compartments and the second portion is folded backwards over the first portion.

21. The container of claim 20, wherein the fold is located between the lower edge of the compartments and the edge between the container side wall and the container bottom wall.

22. The container of claim 17, wherein each compartment is closed with a separate removable cover.

* * * * *